US006187342B1

(12) United States Patent
Zeidler et al.

(10) Patent No.: US 6,187,342 B1
(45) Date of Patent: Feb. 13, 2001

(54) SOLID MEDICAMENTS OBTAINED BY EXTRUSION OF AN ISOMALT-CONTAINING POLYMER-ACTIVE SUBSTANCE MELT

(75) Inventors: Jürgen Zeidler, Mutterstadt; Joerg Rosenberg, Ellerstadt; Jörg Neumann, Limburgerhof; Jörg Breitenbach, Mannheim, all of (DE)

(73) Assignee: BASF Aktiengesellschaft, Ludwigshafen (DE)

( * ) Notice: Under 35 U.S.C. 154(b), the term of this patent shall be extended for 0 days.

(21) Appl. No.: 09/029,362

(22) PCT Filed: Sep. 30, 1996

(86) PCT No.: PCT/EP96/04262

§ 371 Date: Feb. 24, 1998

§ 102(e) Date: Feb. 24, 1998

(87) PCT Pub. No.: WO97/12603

PCT Pub. Date: Apr. 10, 1997

(30) Foreign Application Priority Data

Sep. 29, 1995 (DE) ............................................. 195 36 394

(51) Int. Cl.$^7$ .............................. A61K 9/10; A61K 47/36
(52) U.S. Cl. ............................................ 424/486; 424/488
(58) Field of Search ................................. 424/486

(56) References Cited

FOREIGN PATENT DOCUMENTS

| 240 906 | 10/1987 | (EP) . |
| 354 442 | 2/1990 | (EP) . |
| 95/34293 | 12/1995 | (WO) . |

Primary Examiner—Edward J. Webman
(74) Attorney, Agent, or Firm—Keil & Weinkauf

(57) ABSTRACT

The invention relates to solid drug forms obtainable by extrusion with subsequent shaping of a solvent-free melt, comprising, besides one or more active ingredients, A) 10–90% by weight of a melt-processable, water-soluble polymer, B) 5–85% by weight of isomalt, and C) 0–5% by weight of lecithin, where the total of all the ingredients is to be equal to 100% by weight.

8 Claims, No Drawings

SOLID MEDICAMENTS OBTAINED BY EXTRUSION OF AN ISOMALT-CONTAINING POLYMER-ACTIVE SUBSTANCE MELT

The present invention relates to solid drug forms obtainable by extrusion and subsequent shaping of a solvent-free melt, comprising, besides one or more active ingredients, A) 2–90% by weight of a melt-processable, water-soluble polymer, B) 5–89.9% by weight of isomalt, and C) 0–5% by weight of lecithin, where the stated amounts are based on the total weight of the drug form.

The invention furthermore relates to a process for producing such drug forms.

Formulations containing active ingredients and produced by melt extrusion are generally known.

The extrusion of melts, containing active ingredients, of water-soluble polymers, preferably copolymers of vinylpyrrolidone, is described, for example, in EP-A 240 904 and EP-A 240 906.

The melt extrusion process can be applied to a large number of active ingredients. It is possible specifically to influence the properties of the produced formulations, such as the rate of dissolution of the drug form in the gastrointestinal tract, by using different ancillary substances.

If it is wished to produce solid drug forms with rapid release, it is necessary to use ancillary substances which have a high rate of dissolution in accordance with correspondingly high solubility in water and which, moreover, must not adversely affect the melt-processability of the polymer melt containing active ingredients. Generally employed to date for this purpose have been sugar alcohols such as mannitol or sorbitol or sugars such as lactose.

However, a disadvantage of known compositions is that they are, in some cases, poorly processable, caused by a great tendency to stick during shaping, especially during calendering. In addition, these compositions are frequently still unsatisfactory in respect of release rate. An additional factor is that the lack of mechanical strength of the tablets, because of great embrittlement and thus the occurrence of fissuring, means that improvements are still necessary.

It is an object of the present invention to find drug forms which display rapid release of active ingredient with, at the same time, very good processability and high stability of the drug form.

We have found that this object is achieved by the drug forms defined at the outset.

Suitable active ingredients according to the invention are all those having sufficient thermal stability under the conditions of the melt extrusion process.

Examples of suitable active ingredients are acebutolol, acetylcysteine, acetylsalicylic acid, aciclovir, albrazolam [sic], alfacalcidol, allantoin, allopurinol, ambroxol, amikacin, amiloride, aminoacetic acid, amiodarone, amitriptyline, amlodipine, amoxicillin, ampicillin, ascorbic acid, aspartame, astemizole, atenolol, beclometasone, benserazide, benzalkonium hydrodrochloride [sic], benzocaine, benzoic acid, betametasone, bezafibrate, biotin, biperiden, bisoprolol, bromacepam [sic], bromhexine, bromocriptine, budesonide, bufexamac, buflomedil, buspirone, caffeine, camphor, captopril, carbamazepine, carbidopa, carboplatin, cefaclor, cefalexin, cefatroxil, cefazolin, cefixime, cefotaxime, ceftazidine, ceftriaxone, cefuroxime, celediline [sic], chloramphenicol, chlorhexidine, chlorpheniramine, chlortalidone [sic], choline, ciclosporin, cilastatin, cimetidine, ciprofloxacin, cisapride, cisplatin, claithromycin, clavulanic acid, clomibramine [sic], clonazepam, clonidine, clotrimazole, codeine, colestyramine, cromoglicic acid, cyanocobalamin, cyproterone, desogestrel, dexamethasone, dexpanthenol, dexthromethorphan [sic], dextropropoxiphene, diazepam, diclofenac, digoxin, dihydrocodeine, dihydroergotamine, dihydroergotoxin, diltiazem, diphenhydramine, dipyridamole, dipyrone, disopyramide, domperidonen dopamine, doxocycline [sic], enalapril, ephedrine, epinephrine, ergocalciferol, ergotamine, erythromycin, estradiol, ethinylestradinol, etoposide, Eucalyptus Globulus, famotidine, felodipine, fenofibrate, fenoterol, fentanyl, flavin mononucleotide, fluconazole, flunarizine, fluorouracil, fluoxetine, flurbiprofen, furosemide, gallopamil, gemfibrozil, gentamincin [sic], Ginkgo Biloba [sic], glibenclamide, glipizide, glozapine [sic], Glycyrrhiza Glabra, griseofulvin, guaifenesin, haloperidol, heparin, hyaluronic acid, hydrochlorothiazide, hydrocodone, hydrocortisone, hydromorphone, ibratropium [sic] hydroxide, ibuprofen, imipenem, indomethacin, iohexol, iopamidol, isosorbide dinitrate, isosorbide mononitrate, isotretinion [sic], ketotifen, ketoconazole, ketoprofen, ketorolac, labatalon [sic], lactulose, lecithin, levocarnitine, levodopa, levoglutamide, levonorgestrel, levothyroxine, lidocaine, lipase, lipramine [sic], lisinopril, loperamide, lorazepam, lovastatin, medroxyprogesterone, menthol, methotrexate, methyldopa, methylprednisolone, metoclopramide, metoprolol, miconazole, midazolam, minocycline, minoxidil, misoprostol, morphine, multivitamin and minerals, N-methylephedrine, naftidrofuril, naproxen, neomycin, nicardipine, nicergoline, nicotinamide, nicotine, nicotinic acid, nifedipine, nimodipine, nitrazepam, nitrendipine, nizatidine, norethisterone, norfloxacin, norgestrel, nortriptyline, nystatin, ofloxacin, omeprazole, ondansetron, pancreatin, panthenol, pantothenic acid, paracetamol, penicillin G, penicillin V, phenobarbital, phenoxifylline [sic], phenoxymethylpenicillin, phenylephrine, phenylpropanolamine, phenytoin, piroxicam, polymyxin B, povidone-iodine, pravastatin, prazepam, prazosin, prednisolone, prednisone, promocriptine [sic], propafenone, propranolol, proxyphylline, pseudoephedrine, pyridoxine, quinidine, ramipril, ranitidine, reserpine, retinol, riboflavin, rifampicin, rutoside, saccharin, salbutamol, salcatonin, salicyl [sic] acid, simvastatin, somatropin, sotalol, spironolactone, sucralfate, sulbactam, sulfamethoxazole, sulfasalazine, sulpiride, tamoxifen, tegafur, teprenone, terazosin, terbutaline, terfenadine, tetracycline, theophylline, thiamine, ticlopidine, timolol, tranexamic acid, tretinoin, triamcinolone acetonide, triamterene, trimethoprim, troxerutin, uracil, valproic acid, vancomycin, verapamil, vitamins [sic] E, volinic [sic] acid, zidovudine.

Especially suitable active ingredients according to the invention are those which are suitable for the production of rapid-release forms (instant-release forms).

The preferred active ingredient is verapamil or its physiologically tolerated salts, particularly preferably vearapamil hydrochloride. Paracetamol is also preferred.

Melt-processable, water-soluble polymer components A) which may be mentioned are:

alkylcelluloses such as methylcellulose hydroxymethylcelluloses such as hydroxymethyl-, hydroxyethyl-, hydroxypropyl- and hydroxybutylcellulose, hydroxyalkylmethylcelluloses such as hydroxyethylmethyl- and hydroxypropylmethylcellulose, polyvinylpyrrolidone, copolymers of N-vinylpyrrolidone and vinyl acetate with up to 50% by weight of vinyl acetate, carboxyalkylcelluloses such as carboxymethylcelluloses, polysaccharides such as alginic acid and its alkali metal and ammonium salts, polyethylene glycols and mixtures of such water-soluble polymers.

The component A) should, in the complete mixture of all the components, soften or melt in the range from 50 to 180° C., preferably 80 to 140° C., so that the composition can be extruded. Processability at these temperatures can, where appropriate, be achieved by adding plasticizers.

"Water-soluble" means that at least 0.5 g, preferably at least 2 g, of the polymer dissolves, where appropriate also colloidally, in 100 g of water at 20° C.

Preferred polymer components A) are, besides polyvinylpyrrolidone, the polyethylene glycols and, particularly preferably, a copolymer obtained by free-radical polymerization of 60% by weight of N-vinylpyrrolidone and 40% by weight of vinyl acetate. Hydroxypropylcelluloses are also preferred.

The drug forms contain as an ancillary substance isomalt which is also known under the brand name Palatinit®. Isomalt is a hydrogenated isomaltulose consisting of approximately equal parts of the isomers 1-O-α-D-glucopyranosyl-D-mannitol dihydrate (1,1-GPM dihydrate) and 6-O-α-D-glucopyranosyl-D-sorbitol (1,6-GPS).

The particle size of the isomalt may vary within wide limits, but preferred particle sizes are in the range from 0.1 to 0.8 mm.

The commercially obtainable isomalt is produced by, in a first step, enzymatically rearranging sucrose to isomaltulose (6-O-α-D-glucopyranosyl-D-fructose) and subsequently hydrogenating this isomaltulose with hydrogen/Raney nickel.

The drug forms according to the invention comprise polymer components A) in amounts of from 2 to 90% by weight, preferably 10 to 90% by weight, particularly preferably 10 to 50% by weight. Isomalt is used in amounts of from 5 to 89.9% by weight, preferably 10 to 70% by weight, particularly preferably 20 to 60% by weight.

The amount of the active ingredient also depends on the therapeutic efficacy. It can be incorporated in amounts of from 0.1 to 70, preferably 10 to 60, % by weight, particularly preferably 20 to 50% by weight.

The stated amounts are based in each case on the total weight of the drug form (=100% by weight).

For further improvement of the processing properties, the drug forms may also comprise up to 5% by weight, preferably 2 to 5% by weight, of lecithin.

The formulations according to the invention may furthermore comprise conventional pharmaceutical ancillary substances such as bulking agents, lubricants, mold release agents, flow regulators, plasticizers, dyes and stabilizers in amounts of up to about 50% by weight.

In order to produce the drug forms according to the invention, the active ingredient component can either be directly melted in the form of a physical mixture with the polymers A) or be mixed with the polymer melt which has already been produced.

Otherwise, the active ingredients are mixed with the melt in a conventional way in extruders, preferably in single or twin screw extruders at a temperature in the range from 50 to 180° C., preferably 80 to 140° C. The shaping of the polymer melt containing active ingredient to give the formulations according to the invention can take place, for example, by calendering the extrudate by the method described in EP-A 240 906, and by the process disclosed in DE-A 38 30 355 by converting the extrudate with rotating cutters into blanks which are of equal volume, are still deformable and have a solidified surface, and subsequently compressing to tablets in conventional tabletting machines.

Pellets obtained in this way can, after rounding, also be packed in hard gelatin capsules.

It is possible to mix the ancillary substances into the melt or solution of active ingredients and polymers A). It is furthermore possible for the ancillary substances to be incorporated together with the active ingredient into the polymer melt. Mixtures of ancillary substances, the active ingredient and the polymers can also be directly melted. It is generally customary for a physical mixture of ancillary substances, active ingredients and the polymers to be melted together.

The formulations according to the invention are used as drugs and employed in the form of tablets, pellets, granules or capsules or other drug forms which can be administered orally. Drug forms with rapid release of active ingredient are preferably produced with the formulations according to the invention.

If required, the solid pharmaceutical form can also be provided with a conventional coating to improve the appearance and/or the taste (sugar-coated tablet), or be subjected to a film coating process by spraying on an aqueous or organic polymer solution or dispersion to give film-coated tablets.

It is possible by means of the composition of the drug forms according to the invention to achieve not only rapid release of the active ingredient but also excellent processability.

The problems arising with active ingredients which are particularly prone to stick, such as verapamil hydrochloride, in the handling of the melt and in the shaping are avoided by the formulations according to the invention.

The drug forms described in the following Examples were obtained by the calendering process described in EP-B 240 906. They showed good resistance to mechanical stress and were not prone to tackiness.

EXAMPLES 1 TO 7

Extrusion/calendering—general:

Extruder type: twin screw extruder

Number of sections: 4+head (die)

Tablet shapes: round, lenticular, weight 300 mg

Melt flow: 20–25 kg/h

Determination of release of active ingredient USP XXIII paddle method (verapamil HCl tablets) page 1625

Speed: 50 rpm

Paddle [sic] medium: 0.1 mol/l HCl

The polymer A) used was a copolymer prepared from 60% by weight of N-vinylpyrrolidone and 40% by weight of vinyl acetate ("Copolyvidon" according to the German pharmacopeia).

The stated amounts relate in each case to % by weight.

EXAMPLE 1

Comparative Example

| Verapamil HCl | 26.67% |
|---|---|
| Copolyvidon | 40.00% |
| Mannitol | 28.33% |
| Lecithin | 5.00% |
| Total weight | 363 mg |

Extrusion conditions:

|       | Section 1 | Section 2 | Section 3 | Section 4 | Head |
|---|---|---|---|---|---|
| Temp. (° C.) | 80 | 100 | 115 | 115 | 115 |

The test of release of active ingredient revealed that 52.4% of the active ingredient was released after 30 min.

EXAMPLE 2

| Verapamil HCl | 26.67% |
|---|---|
| Copolyvidon | 40.00% |
| Isomalt | 28.33% |
| Lecithin | 5.00% |
| Total weight | 368 mg |

Extrusion conditions:

|       | Section 1 | Section 2 | Section 3 | Section 4 | Head |
|---|---|---|---|---|---|
| Temp. (° C.) | 100 | 120 | 130 | 130 | 130 |

The test of release of active ingredient revealed that 91.5% of the active ingredient was released after 30 min.

EXAMPLE 3

| Verapamil HCl | 33.33% |
|---|---|
| Copolyvidon | 31.67% |
| Isomalt | 32.00% |
| Lecithin | 3.00% |
| Total weight | 242 mg |

Extrusion conditions:

|       | Section 1 | Section 2 | Section 3 | Section 4 | Head |
|---|---|---|---|---|---|
| Temp. (° C.) | 80 | 100 | 110 | 110 | 110 |

The test of release of active ingredient revealed that 65.4% of the active ingredient was released after 20 min.

EXAMPLE 4

| Verapamil HCl | 33.33% |
|---|---|
| Copolyvidon | 23.67% |
| Isomalt | 40.00% |
| Lecithin | 3.00% |
| Total weight | 246 mg |

Extrusion conditions:

|       | Section 1 | Section 2 | Section 3 | Section 4 | Head |
|---|---|---|---|---|---|
| Temp. (° C.) | 80 | 100 | 110 | 110 | 110 |

The test of release of active ingredient revealed that 77.0% of the active ingredient was released after 20 min.

EXAMPLE 5

| Verapamil HCl | 33.33% |
|---|---|
| Copolyvidon | 13.67% |
| Isomalt | 50.00% |
| Lecithin | 3.00% |
| Total weight | 252 mg |

Extrusion conditions:

|       | Section 1 | Section 2 | Section 3 | Section 4 | Head |
|---|---|---|---|---|---|
| Temp. (° C.) | 80 | 100 | 110 | 110 | 110 |

The test of release of active ingredient revealed that 85.8% of the active ingredient was released after 20 min.

EXAMPLE 6

| Verapamil HCl | 33.33% |
|---|---|
| Copolyvidon | 13.67% |
| Isomalt | 50.00% |
| Lecithin | 3.00% |
| Total weight | 252 mg |

Extrusion conditions:

|       | Section 1 | Section 2 | Section 3 | Section 4 | Head |
|---|---|---|---|---|---|
| Temp. (° C.) | 80 | 100 | 110 | 110 | 110 |

The test of release of active ingredient revealed that 93.2% of the active ingredient was released after 30 min.

EXAMPLE 7

Comparative Example

| Verapamil HCl | 30.00% |
|---|---|
| Copolyvidon | 70.00% |

Extrusion conditions:

| | Section 1 | Section 2 | Section 3 | Section 4 | Head |
|---|---|---|---|---|---|
| Temp. (° C.) | 90 | 130 | 130 | 140 | 140 |

The test of release of active ingredient revealed that 93.7% of the active ingredient was released after 30 min.

EXAMPLE 8

| | | |
|---|---|---|
| Verapamil HCl | | 32% |
| Isomalt | | 41.5% |
| Copolyvidon | | 24% |
| Hydrogenated castor oil | | 2.00% |
| Highly disperse silica | | 0.5% |

| | Section 1 | Section 2 | Section 3 | Section 4 | Head |
|---|---|---|---|---|---|
| Temp. (° C.) | 80 | 100 | 110 | 110 | 110 |

The test of release of active ingredient revealed that at least 96.7% of the active ingredient was released after 30 min.

EXAMPLE 9 AND 10

Paracetamol tablets

Extrusion/calendering—general

Extruder type: twin screw extruder

Tablet shape: oblong, weight 700 mg

Melt flow: 20–25 kg/h

Paddle method: USP 23 [sic] (paracetamol tablets)

The stated amounts relate in each case to % by weight.

EXAMPLE 9

| | |
|---|---|
| Paracetamol | 72% |
| Polyvinylpyrrolidone, K value 30 | 4% |
| Isomalt | 17.25% |
| Highly disperse silica | 1% |
| Sodium starch glycolate | 5% |
| Sodium lauryl sulfate | 0.75% |

| | Section 1 | Section 2 | Section 3 | Section 4 | Head |
|---|---|---|---|---|---|
| Temp. (° C.) | 80 | 120 | 120 | 130 | 145 |

The test of release of active ingredient revealed that 100% of the active ingredient was released after 30 min. Paddle method.

EXAMPLE 10

| | |
|---|---|
| Paracetamol | 72% |
| Copolyvidon | 4% |
| Isomalt | 17.25% |
| Highly disperse silica | 1.00% |
| Sodium starch glycolate | 5% |
| Sodium lauryl sulfate | 0.75% |

-continued

| | Section 1 | Section 2 | Section 3 | Section 4 | Head |
|---|---|---|---|---|---|
| Temp. (° C.) | 80 | 120 | 120 | 130 | 145 |

The test of release of active ingredient revealed that 98% of the active ingredient was released after 30 min.

EXAMPLES 11 TO 13

Vitamim [sic] B complex tablets

Extrusion/calendering—general:

Extruder type: twin screw extruder

Number of sections: 4+head

Tablet shape, round, lenticular, weight about 240 mg Melt flow: 20–25 kg/h

The stated amounts relate in each case to % by weight.

EXAMPLE 11

| | |
|---|---|
| Thiamine mononitrate | 0.572% |
| Riboflavin | 0.704% |
| Pyridoxine HCl | 0.748% |
| Cyanocobalamin (0.1% incorporated in maltodextrin) | 1.32% |
| Calcium D-pantothenate | 2.64% |
| Nicotinic acid | 7.26% |
| Folic acid | 0.066% |
| Biotin | 0.02% |
| Isomalt | 31.67% |
| Hydroxypropylcellulose (Klucel ® EF) | 50.00% |
| Lecithin | 5.00% |

| | Section 1 | Section 2 | Section 3 | Section 4 | Head |
|---|---|---|---|---|---|
| Temp. (° C.) | 80 | 100 | 105 | 105 | 110 |

EXAMPLE 12

| | |
|---|---|
| Thiamine mononitrate | 0.65% |
| Riboflavin | 0.8% |
| Pyridoxine HCl | 0.85% |
| Cyanocobalamin (0.1% incorporated in maltodextrin [sic]) | 1.5% |
| Calcium D-pantothenate | 3.00% |
| Nicotinic acid | 8.25% |
| Folic acid | 0.075% |
| Biotin | 0.015% |
| Isomalt | 45.86% |
| Hydroxypropylcellulose | 35.00% |
| Lecithin | 4% |

| | Section 1 | Section 2 | Section 3 | Section 4 | Head |
|---|---|---|---|---|---|
| Temp. (° C.) | 80 | 90 | 90 | 100 | 115 |

EXAMPLE 13

| | |
|---|---|
| Thiamine mononitrate | 0.3575% |
| Riboflavin | 0.44% |
| Pyridoxine HCl | 0.4583% |
| Calcium D-pantothenate | 1.65% |
| Nicotinamide | 4.537% |
| Biotin | 0.0178% |

-continued

| | | | | |
|---|---|---|---|---|
| Isomalt | | | | 74.538% |
| Hydroxypropylmethylcellulose | | | | 10.00% |
| Kollidon K 30 | | | | 5% |
| Lecithin | | | | 3% |

| | Section 1 | Section 2 | Section 3 | Section 4 | Head |
|---|---|---|---|---|---|
| Temp. (° C.) | 80 | 120 | 130 | 133 | 133 |

We claim:

1. A solid drug form obtained by extrusion with subsequent shaping of a solvent-free melt, comprising, besides one or more active ingredients,
   A) 2–90% by weight of a melt-processable, water-soluble polymer,
   B) 5–89.9% by weight of isomalt, and
   C) 0–5% by weight of lecithin,
where the total of all the ingredients is to be equal to 100% by weight.

2. A drug form as claimed in claim 1, comprising
   A) 10–90% by weight of a melt-processable, water-soluble polymer,
   B) 5–89.9% by weight of isomalt, and
   C) 0–5% by weight of lecithin,
where the total of all the ingredients is to be equal to 100% by weight.

3. A solid drug form as claimed in claim 1, comprising as polymer A) a homo- or copolymer of an N-vinyllactam.

4. A solid drug form as claimed in claim 3, comprising a copolymer of N-vinylpyrrolidone and vinyl acetate.

5. A solid drug form as claimed in claim 1, comprising a hydroxypropylcellulose as polymer A).

6. A solid drug form as claimed in claim 1, comprising as active ingredient verapamil or its physiologically tolerated salts.

7. A solid drug form as claimed claim 1, comprising in addition pharmaceutical ancillary substances.

8. A process for producing drug forms as claimed claim 1, which comprises converting the components into a melt at from 50 to 180° C.

* * * * *